United States Patent
Xiao et al.

(10) Patent No.: US 9,640,386 B2
(45) Date of Patent: May 2, 2017

(54) PRECURSORS FOR CVD SILICON CARBO-NITRIDE FILMS

(71) Applicant: AIR PRODUCTS AND CHEMICALS, INC., Allentown, PA (US)

(72) Inventors: Manchao Xiao, San Diego, CA (US); Arthur Kenneth Hochberg, Solana Beach, CA (US)

(73) Assignee: VERSUM MATERIALS US, LLC, Allentown, PA (US)

( * ) Notice: Subject to any disclaimer, the term of this patent is extended or adjusted under 35 U.S.C. 154(b) by 0 days.

(21) Appl. No.: 14/571,943

(22) Filed: Dec. 16, 2014

(65) Prior Publication Data

US 2015/0147893 A1    May 28, 2015

Related U.S. Application Data

(60) Division of application No. 13/051,591, filed on Mar. 18, 2011, now Pat. No. 8,383,849, and a continuation of application No. 12/267,790, filed on Nov. 10, 2008, now Pat. No. 7,932,413, and a division of application No. 11/129,862, filed on May 16, 2005, now Pat. No. 7,875,556.

(51) Int. Cl.
| | |
|---|---|
| C07F 7/02 | (2006.01) |
| H01L 21/02 | (2006.01) |
| C23C 16/36 | (2006.01) |
| C09D 5/00 | (2006.01) |

(52) U.S. Cl.
CPC ........ *H01L 21/02211* (2013.01); *C07F 7/025* (2013.01); *C09D 5/00* (2013.01); *C23C 16/36* (2013.01); *H01L 21/0228* (2013.01); *H01L 21/02167* (2013.01); *H01L 21/02219* (2013.01); *H01L 21/02222* (2013.01); *H01L 21/02271* (2013.01); *H01L 21/02274* (2013.01)

(58) Field of Classification Search
CPC ...................................................... C07F 7/025
USPC .................................. 556/410, 412; 544/229
See application file for complete search history.

(56) References Cited

U.S. PATENT DOCUMENTS

| | | | |
|---|---|---|---|
| 4,200,666 A | 4/1980 | Reinberg | |
| 5,008,422 A | 4/1991 | Blum et al. | |
| 5,234,869 A | 8/1993 | Mikata et al. | |
| 5,250,473 A | 10/1993 | Smits | |
| 5,382,550 A | 1/1995 | Iyer | |
| 5,458,689 A | 10/1995 | Saito | |
| 5,622,784 A | 4/1997 | Okaue et al. | |
| 5,656,076 A | 8/1997 | Kikkawa | |
| 5,772,757 A | 6/1998 | Saito | |
| 5,837,056 A | 11/1998 | Kikkawa | |
| 5,874,368 A | 2/1999 | Laxman et al. | |
| 5,976,991 A | 11/1999 | Laxman et al. | |
| 6,153,261 A | 11/2000 | Xia et al. | |
| 6,391,803 B1 | 5/2002 | Kim et al. | |
| 6,486,015 B1 | 11/2002 | Chaudhary et al. | |
| 6,500,772 B2 | 12/2002 | Chakravarti et al. | |
| 6,630,413 B2 | 10/2003 | Todd | |
| 6,963,006 B2 | 11/2005 | Tsui et al. | |
| 6,974,780 B2 | 12/2005 | Schuegraf | |

(Continued)

FOREIGN PATENT DOCUMENTS

| | | |
|---|---|---|
| EP | 0 481 706 A1 | 4/1992 |
| EP | 1149934 | 8/2005 |

(Continued)

OTHER PUBLICATIONS

Gary E. McGuire, Semiconductor Materials and Process Technology Handbook, Noyes Publications, NJ, 1988, pp. 239-301.

Stanley Wolf, Silicon Processing for the VLSI Era, Lattice Press, CA 1990, pp. 327-330.

Arthur K. Hochberg, et al, Diethylsilane as a Source for the Deposition . . . , Mat. Res. Soc, Symp. Proc., vol. 204, 1991, pp. 509-513.

Tetsuji Sorita, et al, Mass Spectrometric and Kinetic Study of Low-Pressure . . . , J. Elec. Soc., vol. 141, No. 12, 1994, pp. 3506-3511.

(Continued)

*Primary Examiner* — Porfirio Nazario Gonzalez
(74) *Attorney, Agent, or Firm* — Michael K. Boyer

(57) ABSTRACT

Classes of liquid aminosilanes have been found which allow for the production of silicon carbo-nitride films of the general formula $Si_xC_yN_z$. These aminosilanes, in contrast, to some of the precursors employed heretofore, are liquid at room temperature and pressure allowing for convenient handling. In addition, the invention relates to a process for producing such films.

The classes of compounds are generally represented by the formulas:

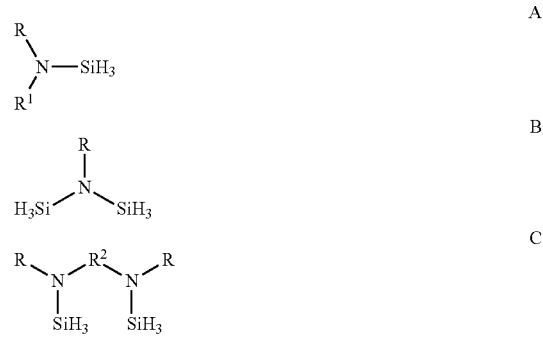

and mixtures thereof, wherein R and $R^1$ in the formulas represent aliphatic groups typically having from 2 to about 10 carbon atoms, e.g., alkyl, cycloalkyl with R and $R^1$ in formula A also being combinable into a cyclic group, and $R^2$ representing a single bond, $(CH_2)_n$, a ring, or $SiH_2$.

18 Claims, 3 Drawing Sheets

(56) References Cited

U.S. PATENT DOCUMENTS

| | | | |
|---|---|---|---|
| 7,098,150 | B2 | 8/2006 | Misra et al. |
| 7,482,286 | B2 | 1/2009 | Misra et al. |
| 7,825,040 | B1 | 11/2010 | Fukazawa et al. |
| 2002/0175393 | A1 | 11/2002 | Baum et al. |
| 2002/0180028 | A1 | 12/2002 | Borovik et al. |
| 2004/0146644 | A1 | 7/2004 | Xiao et al. |
| 2004/0194706 | A1 | 10/2004 | Wang et al. |
| 2005/0025885 | A1 | 2/2005 | McSwiney et al. |
| 2005/0163927 | A1 | 7/2005 | McSwiney et al. |
| 2006/0051975 | A1 | 3/2006 | Misra et al. |
| 2006/0099831 | A1 | 5/2006 | Borovik et al. |
| 2006/0258173 | A1 | 11/2006 | Xiao et al. |
| 2006/0286774 | A1 | 12/2006 | Singh et al. |
| 2007/0004931 | A1 | 1/2007 | Xiao et al. |
| 2007/0275166 | A1 | 11/2007 | Thridandam et al. |
| 2009/0069588 | A1 | 3/2009 | Xiao et al. |
| 2009/0075490 | A1 | 3/2009 | Dussarrat |
| 2010/0009546 | A1 | 1/2010 | Weigel et al. |
| 2010/0041243 | A1 | 2/2010 | Cheng et al. |
| 2013/0078376 | A1 | 3/2013 | Higashino et al. |
| 2013/0330937 | A1 | 12/2013 | Xiao et al. |

FOREIGN PATENT DOCUMENTS

| | | |
|---|---|---|
| GB | 1123252 | 8/1968 |
| JP | 6132276 | 5/1994 |
| JP | 06132284 | 5/1994 |
| JP | 07235535 | 9/1995 |
| JP | 00195801 | 7/2000 |
| JP | 2001156063 | 6/2001 |
| JP | 200526244 | 1/2005 |
| KR | 1020050018641 | 2/2005 |
| KR | 1020050018641 | 2/2006 |
| WO | 200265508 | 8/2002 |
| WO | 02079211 | 10/2002 |
| WO | 2004010467 | 1/2004 |
| WO | 2004017383 | 2/2004 |
| WO | 2004030071 | 4/2004 |
| WO | 2005080628 | 9/2005 |
| WO | 2005093126 | 10/2005 |
| WO | 2006033699 | 3/2006 |
| WO | 2006036538 | 4/2006 |
| WO | 2006097525 | 9/2006 |

OTHER PUBLICATIONS

B.J. Aylett, et al, The Preparation and Properties of Dimethylamino- and . . . , J. Chem. Soc. (A), 1967, pp. 652-655.

Sei Sujishi, et al, Effect of Replacement of Carbon by Silicon in Trimethylamine . . . , J. Am. Chem. Soc., vol. 78, 1956, pp. 4631-4636.

Kenneth Hedberg, The Molecular Structure of Trisilylamine (SiH3) 3N1, 2, J. Am. Chem. Soc., 1955, vol. 77, pp. 6491-6492.

J.M. Grow, et al, Growth Kinetics and Characterization of Low Pressure . . . , Mat. Letters vol. 23, 1995, pp. 187-193.

B.A. Scott, et al, Preparation of Silicon Nitride with Good Interface . . . , Chemtronics, 1989, vol. 4, pp. 230-233.

B.J. Aylett, et al, Silicon-Nitrogen Compounds. Part V. Diphenylamino-derivatives of Silane, J. Chem. Soc., 1989, 636-639.

Norbert W. Mizel, Simple Silylhydrazines as Models for Si—N. beta.-donor Interactions in SiNN Units, Chemistry—A European Journal, 1998, 692-698.

Hubert Schmidbuar, et al, Differences in Reactivity of 1,4-Disilabutane and N-Tetrasilane Towards Secondary Amines, Zeitschrift Fur Naturforschung B: Chemical Sciences, 1990, 1679-1683.

A.V. Golubinszkij, et al, Molecular-structure Examination of Some Organic Silicon Compounds by Electron Diffraction, Kemiai Kozlemenyek, 46, 1976, 473-480.

C. Glidewell, et al, Electron Diffraction Determination of the Molecular Structure of Tetrasilylhydrazine, Journal of the Chemical Society, 1970, 318-320.

H. Beck, et al, Radical Ions. 36. Structural Changes Accompanying the One-Electron Oxidation of Hydrazine and Its Silyl Denvatives1-3, Journal of the American Chemical Society, 1980, 4421-4428.

B.J. Aylett, The Silyl Group as an Electron Acceptor, J. Inorg. Nucl. Chem., 1956, 325-329.

N. Bingo, et al, Correlations Among X-H Bond Lengths, X-H Stretching Frequencies, and Bond Order Matrix Elements P HX: where X=C, N, and Si, J. Sci. Hiroshima Univ., 1976, 317-326.

B.J. Aylett, Vibrational spectra and structure of tetrasilylhydrazine and tetrasilylhydrazine-d, Spectrochimica Acta, 1960, 747-758.

C. Glidewell, et al, Some Preparative and Spectroscopic Studies of Silylamines, Journal of the Chemical Society A Inorg. Phys. Theor, 1970, 279-286.

B.J. Aylett, et al, N-Silyl Derivatives of Cyclic Secondary Amines, J. Chem. Soc, 1967, 1918-1921.

B.J. Aylett, et al, Silicon-Nitrogen Compounds. Part VIII. Base-Promoted Disproportionation of N-Methly- and N-Phenyl-Disilazane, J. Chem. Soc., 1969, 1788-1792.

D. Anderson, et al, Isopropyldisilylamine and Disilyl-t-butylamine: Preparation, Spectroscopic Properties, and Molecular Structure in the Gas Phase, determined by Electron Diffraction, J. Chem. Soc., 1989, 779-783.

Dussarrat, C., et al, "Low Pressure Chemical Vapor Deposition of Silicon Nitride Using Mono- and Disilylamine", The 203rd Meeting Proceeding of ECS, Apr. 27, 2003.

Rakin, D.W.H., et al, "8. Gas-phase Molecular Structures Determined by Electron Diffraction", Spectroscopic Properties of Inorganic and Organometallic Compounds, vol. 23, The Royal Society of Chemistry, Thomas Graham House, 1990.

Mui, C., et al, "Surface reaction mechanisms for atomic layer deposition of silicon nitride", Surface Science, vol. 557, pp. 159-170, Mar. 16, 2004.

V. Passarelli, Aminolysis of the Si—Cl bond and ligand exchange reaction between silicon amido derivatives and SiCl4: synthetic applications and kinetic investigations, The Royal Society of Chemistry, 2003, 413-419.

T. Shibata, et al, "ALD-SiO2 Deposition and CD Slimming Techniques for Double Patterning and a Heater-less Batch Tool", Semiconductor Manufacturing (ISSM), 2010 International Symposium, 1-3.

Paprotta, S.; "Untersuchung von Silizium- und Germanium-Nano-Clustern fuer die moderne Speichertechnologie"; Disseration Universitaet Hannover; Jan. 1, 2005; pp. 1-34.

Wrobel, Aleksander, et al, "Silicon Carbonitride (SiCN) Films by Remote Hydrogen Microwave Plasma CVD from Tris(dimethylamino)silane as Novel Single-Source Precursor", Chemical Vapor Deposition, 2010, 211-215.

Chiang, Justin, et al, "Plasma Deposited Silicon Nitride Film Chemistry", Mat. Res. Soc. Symp. Proce, 1990, 79-84.

PRECURSORS FOR CVD SILICON CARBO-NITRIDE FILMS

CROSS REFERENCE TO RELATED APPLICATIONS

The present patent application is a divisional application of U.S. patent application Ser. No. 13/051,591, which was filed on Mar. 18, 2011 and is now issued U.S. Pat. No. 8,383,849, which was a continuation of U.S. patent application Ser. No. 12/267,790, filed Nov. 10, 2008, and is now issued U.S. Pat. No. 7,932,413, which was a divisional application U.S. patent application Ser. No. 11/129,862, filed May 16, 2005 and is now issued U.S. Pat. No. 7,875,556.

BACKGROUND OF THE INVENTION

In the fabrication of semiconductor devices, a thin passive layer of a chemically inert dielectric material such as, silicon nitride ($Si_3N_4$) or silicon carbo-nitride ($Si_xC_yN_z$) is essential. Thin layers of silicon nitride function as diffusion masks, oxidation barriers, trench isolation, intermetallic dielectric material with high dielectric breakdown voltages and passivation layers. Many applications for silicon nitride coatings in the fabrication of semiconductor devices are reported elsewhere, see Semiconductor and Process technology handbook, edited by Gary E. McGuire, Noyes Publication, New Jersey, (1988), pp 289-301; and Silicon Processing for the VLSI ERA, Wolf, Stanley, and Talbert, Richard N., Lattice Press, Sunset Beach, Calif. (1990), pp 20-22, 327-330.

Many of the new semiconductor devices require dielectric films that have very low etch rates or very high film stresses, or both. It is also preferred, and sometimes necessary, that the films be formed at temperatures below 600° C. while maintaining good electrical characteristics. Film hardness is another factor to consider in the design of the electrical components and the silicon nitride films do offer extremely hard films.

One of the commercial methods for forming silicon nitride coatings employs dichlorosilane and ammonia as the precursor reactants. Low pressure chemical vapor deposition (LPCVD) using precursors such as dichlorosilane and ammonia require high deposition temperatures to get the best film properties. For example, temperatures greater than 750° C. may be required to obtain reasonable growth rates and uniformities. Other processing issues involve the hazardous aspects of chlorine and chlorine byproducts.

The following articles and patents are cited as representative of the art with respect to the synthesis of organosilanes and deposition processes employed in the electronics industry.

A. K. Hochberg and D. L. O'Meara, *Diethylsilane as a Silicon Source for the Deposition of Silicon Nitride and Silicon Oxynitride Films By LPCVD*, Mat. Res. Soc. Symp. Proc., Vol. 204, (1991), pp 509-514, disclose the formation of silicon nitride and silicon oxynitride films using diethylsilane with ammonia and nitric oxide by LPCVD. The deposition is carried out in a temperature range of 650° C. to 700° C. The deposition is limited generally to a temperature of 650° C. as the deposition rate drops to below 4 ANG./min at lower temperatures.

Sorita et al., *Mass Spectrometric and Kinetic Study of Low-Pressure Chemical Vapor Deposition of $Si_3N_4$ Thin Films From $SiH_2Cl_2$ and $NH_3$*, J. Electro. Chem. Soc., Vol. 141, No. 12, (1994), pp 3505-3511, describe the deposition of silicon nitride using dichlorosilane and ammonia using a LPCVD process. The formation of ammonium chloride leads to particle formation and deposition of ammonium chloride at the backend of the tube and in the plumbing lines and the pumping system.

Aylett and Emsley, *The Preparation and Properties of Dimethylamino and Diethylamino Silane*, J. Chem. Soc. (A) p 652-655, 1967, disclose the preparation of dimethylamino and diethylaminosilane by the reaction of iodosilane with the respective dialkyl amine.

Anderson and Rankin, *Isopropyldisilylamine and Disilyl-t-butylamine: Preparation, Spectroscopic Properties, and Molecular Structure in the Gas Phase, Determined by Electron Diffraction*, J. Chem. Soc. Dalton Trans., p 779-783 1989 disclose the synthesis of disilyl amines of the formula $NR(SiH_3)_2$, e.g., isopropyldisilylamine and disilyl-t-butylamine and they provide spectroscopic comparisons to the corresponding methyldisilylamine.

Japanese Patent 6-132284 describes the formation of silicon nitride films using organosilanes having a general formula $(R_1R_2N)_nSiH_{4-n}$, (where $R_1$ and $R_2$ range from H—$CH_3$—, $C_2H_5$—$C_3H_7$—, $C_4H_9$—) by either a plasma enhanced chemical vapor deposition or thermal chemical vapor deposition in the presence of ammonia or nitrogen.

U.S. Pat. No. 5,234,869 discloses the formation of a silicon nitride film by CVD using $Si(N(CH_3)_2)_4$ and ammonia as reactant gases. A chamber temperature of 700° C. and a pressure of 0.5 Torr was used for the deposition. Other reactants selected from the group consisting of $SiH(N(CH_3)_2)_3$, $SiH_2(N(CH_3)_2)_2$, and $SiH_3(N(CH_3)_2)$ in combination with ammonia or nitrogen were also suggested as reactants. It was also disclosed that plasma produced by radiating the gas with an ultra-violet beam, the temperature was decreased to 300° C.

U.S. Pat. No. 5,874,368 teaches the use of bis(tertiary-butylamino)silane as a precursor to deposit silicon nitride using low pressure chemical vapor deposition at a temperature range of 500° to 800° C.

U.S. Pat. No. 5,874,368 and U.S. Pat. No. 6,153,261 disclose the formation of silicon nitride films using bis(tertiarybutylamino)silane as a silicon reactant gas. LPCVD is used to generate the film.

U.S. Pat. No. 6,391,803 discloses the formation of silicon containing thin films by atomic layer deposition using a silane of the formula $Si(N(CH_3)_2)_4$, $SiH(N(CH_3)_2)_3SiH_2(N(CH_3)_2)_2SiH_3(N(CH_3)_2)$, preferably trisdimethylaminosilane, as a first reactant. A portion of the first reactant is chemisorbed onto the substrate and a second portion is physisorbed onto the substrate. The reactant is purged and a second reactant, i.e., $NH_3$ is introduced.

BRIEF SUMMARY OF THE INVENTION

Classes of liquid aminosilanes have been found which allow for the production of silicon carbo-nitride films of the general formula $Si_xC_yN_z$ by CVD processes. These aminosilanes, in contrast to some of the precursors employed heretofore, are liquid at room temperature and pressure and allow for convenient handling. In addition, the invention relates to a deposition process for producing such films.

The classes of compounds are generally represented by the formulas:

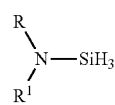

A

-continued

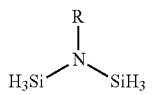
B

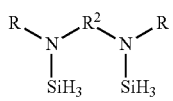
C and mixtures thereof, wherein R is selected from $C_1$-$C_{10}$ alkyl groups, linear, branched, or cyclic, saturated or unsaturated; aromatic, heterocyclic, or silyl in formula C, $R^1$ is selected from $C_2$-$C_{10}$ alkyl groups, linear, branched, or cyclic, saturated or unsaturated; aromatic, heterocyclic, hydrogen, silyl groups with or without substituents with R and $R^1$ in formula A also being combinable into a cyclic group $(CH_2)_n$, wherein n is from 1-6, preferably 4 and 5 and $R^2$ representing a single bond, $(CH_2)_n$ chain, a ring, $SiR_2$, or $SiH_2$. Preferred compounds are such that both R and $R^1$ have at least 2 carbon atoms. The classes of compounds are generally represented by the formulas:

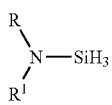
A

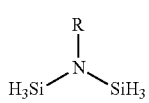
B

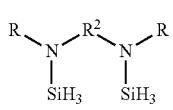
C and mixtures thereof, wherein R and $R^1$ in the formulas represent aliphatic groups typically having from 2 to about 10 carbon atoms, e.g., alkyl, cycloalkyl with R and $R^1$ in formula A also being combinable into a cyclic group, and $R^2$ representing a single bond, $(CH_2)_n$, a ring, or $SiH_2$.

The precursors employed in CVD processes can achieve many advantages, and these include:

an ability to facilitate formation of dielectric films at low thermal conditions without incurring the problems of plasma deposition;

an ability to mix the aminosilanes with other precursors, e.g., ammonia at various stoichiometries, for permitting control of the ratio of Si—C bonds to Si—N bonds and thereby control the characteristics of the resulting films;

an ability to produce films having high refractive indices and film stresses;

an ability to produce films having low acid etch rates;

an ability to produce films of high densities;

an ability to generate films while avoiding chlorine contamination; and, an ability to operate at low pressures (20 mTorr to 2 Torr) in a manufacturable batch furnace (100 wafers or more); and, an ability to generate $Si_xC_yN_z$ films at low temperatures, e.g., as low as 550° C. and below.

DETAILED DESCRIPTION OF THE INVENTION

Figure 1:
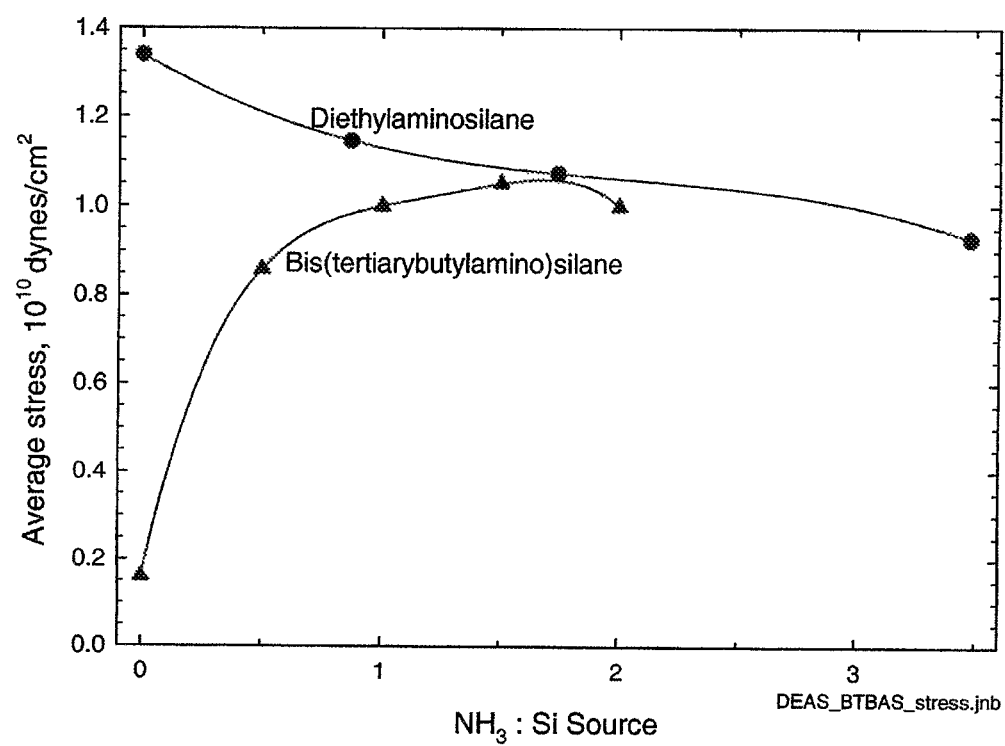
FIG. 1 is a plot of the stress values for films formed by the deposition of diethylaminosilane and bis(tertiary)butylamino)silane as a function of the mole ratio of $NH_3$ to precursor in the deposition process.

It has been found that classes of liquid organo aminosilanes having an N—$SiH_3$ group as a key feature in the molecular structure are suitable as precursors for producing silicon carbo-nitride films via CVD in the electronics industry. These compounds lend themselves to the production of $Si_xC_yN_z$ films under a variety of conditions.

The compounds herein are liquid at atmospheric pressure and room temperature, i.e., 25° C. and thus provide a significant advantage over the reported usage of the trimethyl substituted aminosilane. They are substituted with organo groups having at least 2 carbon atoms in the chain on the amino group providing for stability under conventional handling and processing conditions.

One class of amino silane is resented by formula A as follows:

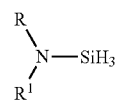
A

In this class of compounds R is selected from $C_1$-$C_{10}$ alkyl groups, linear, branched, or cyclic, saturated or unsaturated; aromatic, heterocyclic. $R^1$ is selected from $C_2$-$C_{10}$ alkyl groups, linear, branched, or cyclic, saturated or unsaturated; aromatic, heterocyclic, hydrogen, silyl groups, with or without substituents, and R and $R^1$ also being combinable into a cyclic group. Representative substituents are alkyl groups and particularly the $C_{2-4}$ alkyl groups, such as ethyl, propyl and butyl, including their isomeric forms, cyclic groups such as cyclopropyl, cyclopentyl, and cyclohexyl. Illustrative of some of the preferred compounds within this class are represented by the formulas:

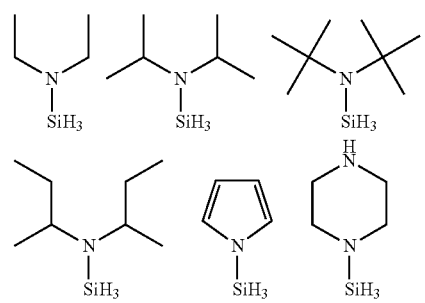

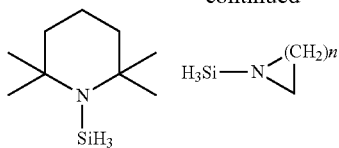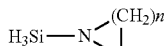

where n is 1-6, preferably 4 or 5.

The second class of aminosilane has two silyl groups pendant from a single nitrogen atom as represented by formula B.

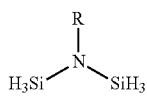

B

As with the R groups of the Class A compounds, R is selected from $C_2$-$C_{10}$ alkyl groups, linear, branched, or cyclic, saturated or unsaturated; aromatic, heterocyclic. Specific R groups include methyl, ethyl, propyl, allyl, and butyl; and cyclic groups such as cyclopropyl, cyclopentyl, and cyclohexyl. Illustrative compounds are represented by the formulas:

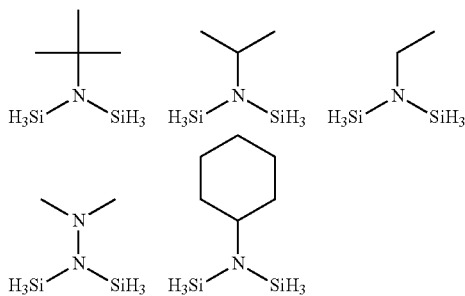

The third class of aminosilane compound is represented by formula C. These are generally diaminodisilyl compounds with R is same as R and $R^1$ in formulas A and the $R^2$ group bridging the nitrogen atoms. Sometimes the $R^2$ group is nothing more than a single bond between the nitrogen atoms or it may be a bridging group, such as $SiR_2$, $SiH_2$, a chain, or a ring. The formula is as follows:

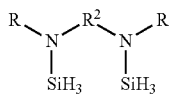

C

Specific examples include those represented by the formulas:

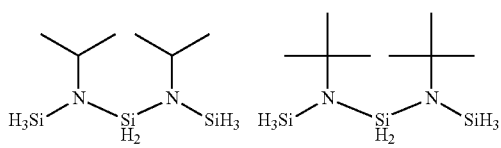

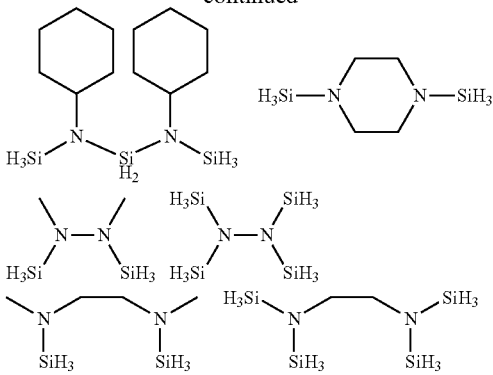

These compounds are synthesized in general by the following reactions, which are also demonstrated by Examples 1, 2, 3, and 4.

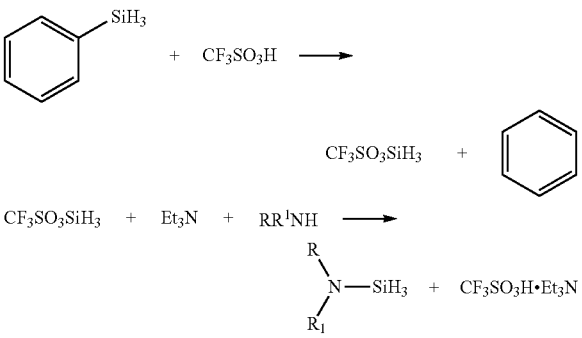

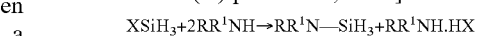

Although the above series of reactions illustrate a route to the aminosilanes as described, other sources of a silane precursor may be used. This route allows for a rather straight forward control as to whether mono and disilyl compounds are produced using the reaction stoichiometry and the use of a wide variety of amines.

Some of these compounds can also be synthesized by the reaction of monohalosilanes with corresponding amines, as described in *The Preparation and Properties of Dimethylamino and Diethylamino Silane* [Aylett and Emsley, J. Chem. Soc. (A) p 652-655, 1967].

$XSiH_3 + 2RR^1NH \rightarrow RR^1N-SiH_3 + RR^1NH \cdot HX$

Representative amines well suited for the reaction are the alkyl, cyclic, and heterocyclic. Preferred amines are the lower alkyl amines, e.g., ethyl, iso-propyl, t-butyl, and cyclohexyl. Further the amines may be primary or secondary depending upon the product desired.

In the formation of silicon carbo-nitride films, the mono or diaminosilanes, optionally with ammonia or nitrogen source, are allowed to react in a deposition chamber at conventional deposition temperatures. Such films may be formed in deposition chambers designed for chemical vapor deposition (CVD), low pressure chemical vapor deposition (LPCVD) plasma enhanced CVD (PECVD), atomic layer deposition (ALD), and so forth. The term CVD as used herein is intended to include each of these processes which are employed in semiconductor deposition.

As stated in the advantages, the liquid aminosilanes described herein, in many cases offer the fabricator the ability to form silicon carbo-nitride films via CVD at relatively low temperatures, although a general temperature range is from 500 to 700° C. Unexpectedly, $Si_xC_yN_z$ film deposition can be achieved presumably because of the high activity of the $SiH_3$ group(s). It is believed the low steric hindrance for the ammonia transamination reaction on the silicon center, allows these compounds to react with ammonia and deposit films with increasing nitrogen concentrations at relatively low temperatures.

The deposition of the aminosilane precursors may be carried out in the absence of, or in the presence of, an active nitrogen source such as hydrazine, dimethylhydrazine, or ammonia. Molar ratios of the nitrogen source to aminosilane generally are broadly within the range of from 0: to >10:1. The upper limit is restricted by the dilution effect on the precursor and the dilution effect will significantly diminish the deposition rate. Preferred ranges are from 0.1 to 4:1. The formation of films via deposition may also be carried out with or without other gases including with inert gases, such as nitrogen and helium. The use of gases by the fabricator to achieve corresponding dilution of the precursor may improve the conformality of the deposition or improve the penetration for chemical vapor infiltration.

Low pressure chemical vapor deposition processes (LPCVD) involve chemical reactions that are allowed to take place on a variety of substrates, e.g., silicon, within a pressure range of 20 mTorr to 20 Torr. High pressure CVD may result in gas phase nucleation or predeposition before the desired substrate is reached. Dilution of the aminosilane precursor may be required for such high pressure reactions. Low pressure deposition with some of the aminosilane precursors may exhibit rates of deposition to non-commercially usable levels. However, such aminosilanes may be suitable for atomic layer deposition.

In carrying out deposition processes, the aminosilanes described herein can be blended with other silyl precursors to alter film properties. Examples of other precursors include bis-tert-butylaminosilane, tris-iso-propylaminosilane, bis-diethylaminosilane, tris-dimethylaminosilane, and bis-iso-propylaminosilane.

The following examples are intended to illustrate various embodiments of the invention including the synthesis of various silanes and the LPCVD of silicon carbo nitride film forming precursors.

Example 1

Synthesis of Diethylaminosilane 50 grams (0.33 mol) of trifluoromethanesulfonic acid and 100 ml of toluene were added to a 250 ml flask. Under the protection of nitrogen, the flask was cooled to −40° C. 40.6 grams (0.33 mol) of tolylsilane was added slowly. Then the flask was cooled to −60° C. 33.5 grams of triethylamine was added slowly, followed by addition of 24 grams of diethylamine. After addition, the temperature of the flask was allowed to warm to room temperature gradually. Two layers of liquid were formed. The upper layer was separated using a separation funnel. 25 grams of diethyaminolsilane was obtained by vacuum distillation. The boiling point of the diethyaminolsilane was 40-42° C. at 210 mmHg.

Example 2

Synthesis of Di-Iso-Propylaminosilane 50 grams (0.33 mol) of trifluoromethanesulfonic acid and 80 ml of pentane were added to a 250 ml flask. Under the protection of nitrogen, the flask was cooled to −40° C. 35.6 grams (0.33 mol) of phenylsilane was added slowly. Then the flask was cooled to −60° C. 33.3 grams (0.33 mol) of triethylamine was added slowly, followed by addition of a solution 33.3 grams (0.33 mol) of di-iso-propylamine in 15 ml of pentane. After addition, the temperature of the flask was allowed to warm to room temperature gradually. Two layers of liquid were formed. The upper layer was separated using a separation funnel. The solvent and by product benzene were removed by distillation. 30 grams of di-iso-propylaminosilane was obtained by vacuum distillation. The boiling point of the di-iso-propylaminosilane was 55° C. at 106 mmHg.

Example 3

Synthesis of Cyclohexyldisilylamine and 2,4-Dicyclohexyl-2,4-Diaza-1,3,5-Trisilapentane 62.5 grams of trifluoromethanesulfonic acid and 100 ml of pentane were added to a 500 ml flask. Under the protection of nitrogen, the flask was cooled to −40° C. 45 grams of phenylsilane was added slowly. Then the flask was cooled to −60° C. 42 grams of triethylamine was added slowly, followed by addition of a solution 20.6 grams of cyclohexylamine in 15 ml of pentane. After addition, the temperature of the flask was allowed to warm to room temperature gradually. Two layers of liquid were formed. The upper layer was separated using a separation funnel. The solvent and by product benzene were removed by distillation. 15 grams of cyclohexyldisilylamine was obtained by vacuum distillation. The boiling point of the cyclohexyldisilylamine was 54-55° C. at 17 mmHg. The remaining high boiling point portion contains 96.6% 2,4-dicyclohexyl-2,4-diaza-1,3,5-trisilapentane.

Example 4

Synthesis of Cyclohexyldisilylamine and 2,4-Di-Tert-Butyl-2,4-Diaza-1,3,5-Trisilapentane 50.0 grams (0.33 mol) of trifluoromethanesulfonic acid and 100 ml of pentane were added to a 500 ml flask. Under the protection of nitrogen, the flask was cooled to −40° C. 35.6 grams (0.33 mol) of phenylsilane was added slowly. Then the flask was cooled to −60° C. 33.3 grams (0.33 mol) of triethylamine was added slowly, followed by addition of a solution 28.7 grams (0.165 mol) of bis-t-butylaminosilane in 15 ml of pentane. After addition, the temperature of the flask was allowed to warm to room temperature gradually. Two layers of liquid were formed. The upper layer was separated using a separation funnel. The solvent and by product benzene were removed by distillation. 21 grams of 2,4-di-tert-butyl-2,4-diaza-1,3,5trisilapentane was obtained by vacuum distillation.

Example 5

Formation of Silicon Carbo Nitride Film Using Diethylaminosilane Precursor

General Procedure

The aminosilane precursors are tested in an LPCVD reactor used to qualify experimental precursors for silicon carbo-nitride depositions. The precursors are degassed and metered into the reactor through a low-pressure mass flow controller (MFC) as required. The MFC flows are calibrated against weight losses of the chemicals vs. time of flow.

Additional reactants, such as ammonia, and diluents, such as nitrogen and helium, as specified are also metered into the reactor through calibrated MFCs, as required. The reactor is connected to a roots blower/dry pump combination capable of evacuating the reactor to below $10^{-4}$ Torr (0.013 Pa). The temperature across a load of silicon wafers, during deposition, is within 1° C. of the set point.

Silicon wafers are loaded onto a quartz boat and inserted in the reactor. The reactor is pumped to base pressure and checked for leaks. The system is ramped to the process temperature with gas flows that would dilute any residual oxygen or moisture to prevent any oxidation of the silicon wafers as the reactor heats up. The reactor is then stabilized for a predetermined time to bring all wafer surfaces to an equal temperature (as had been determined by previous measurements on wafers with attached thermocouples).

The gases and vapors are injected into the reactor for a predetermined deposition time at a controlled pressure. Next, the gases are shut off, and the reactor is pumped to a base pressure. The reactor, then, is pump-purged, pumped down, and pump-purged to clear any reactive gases or vapors as the reactor is cooled down. The reactor is backfilled to atmospheric pressure; the wafers are removed and allowed to cool to room temperature. The deposited films are then measured for film thickness, film refractive index, film stress (FIG. 1), infrared absorbances (shown in FIG. 3), dielectric constant, and acid etch rate (Table 1).

In forming the deposited films, 10 sccm of diethylaminosilane (DEAS) was flowed into a reactor at 570° C. along with 20 sccm $NH_3$ and 20 sccm $N_2$ at 1.3 Torr (173.3 Pa) for a deposition time of 60 minutes.

The average film thickness was 69 nm and refractive index was 2.045. The film stress was measured as $1.07 \times 10^{10}$ dynes/cm$^2$ (1.07 GPa).

Figure 3:
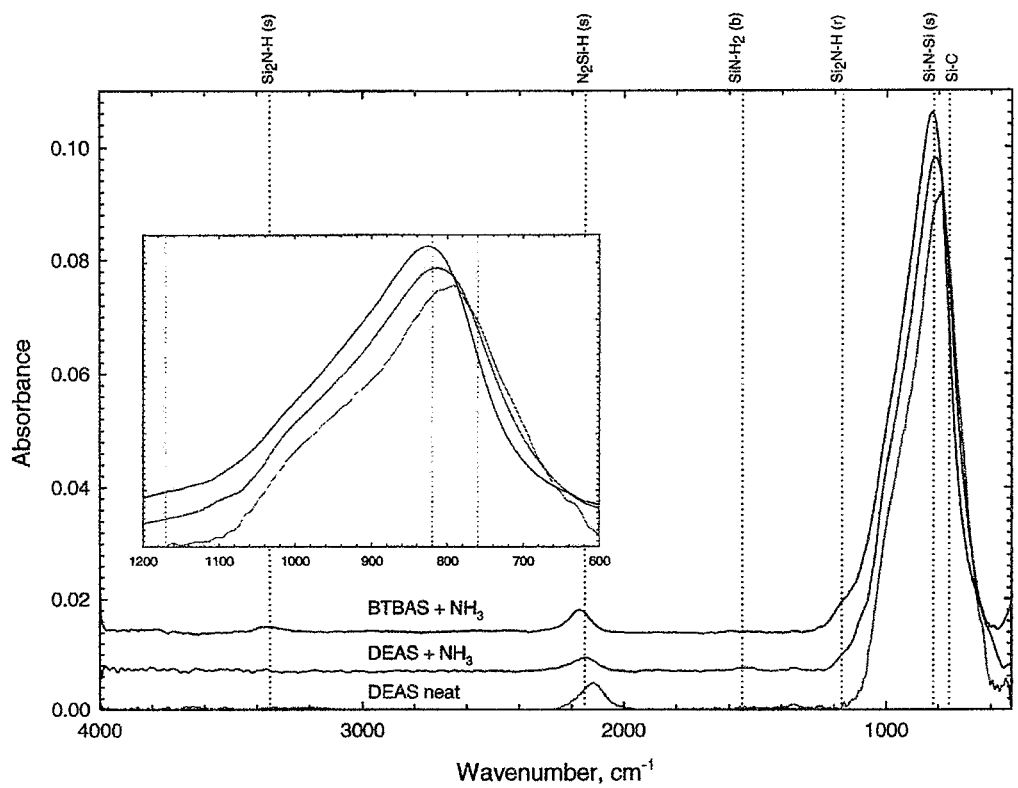
FIG. 3 is a plot of the infrared spectra ion of films generated by the deposition of diethylaminosilane (neat), diethylaminosilane with $NH_3$ and bis(tertiary)butylamino) silane.

The infrared spectra were dominated by Si—C and Si—N absorptions. C—H or C—N absorptions were in the noise illustrating, as shown in FIG. 3, the film composition was largely in the form of $Si_xC_yN_z$ as is desired.

Example 6

Formation of Silicon Carbo-Nitride Film Using Diethylaminosilane Precursor Using $N_2$ without $NH_3$ The procedure of Example 4 was followed with the exception of process conditions. Nitrogen was used in place of $NH_3$. In this example, 10 sccm of diethylaminosilane (DEAS) was flowed into a reactor at 600° C. with 40 sccm $N_2$ at 1.0 Torr (133 Pa) for a deposition time of 40 minutes.

The average film thickness was 42 nm and refractive index was 2.288. The film stress was measured as $1.34 \times 10^{10}$ dynes/cm$^2$. These films have even higher stresses and lower etch rates than those obtained with ammonia (See Table 1 for etch rates). The conformalities of such films were found to be 100% on isolated structures.

Example 7

Formation of Silicon Carbo-Nitride Film Using Diisopropylaminosilane Precursor Using $N_2$ without $NH_3$ The procedure of Example 5 was followed with the exception of the precursor. 10 sccm of diisopropylaminosilane (DIPAS) was flowed into a reactor at 570° C. with 20 sccm He and 20 sccm $N_2$ at 1.0 Torr (133 Pa) for a deposition time of 70 minutes.

The average film thickness was 46 nm and refractive index was 2.056. The film stress was measured as $1.07 \times 10^{10}$ dynes/cm$^2$. Surprisingly, the refractive index and stress were similar for diisopropylaminosilane to that of the precursor of Example 6. These results show excellent stress values within this class of materials can be achieved.

Example 8

Formation of Silicon Carbo-Nitride Film Using Bis(Tertiary Butylamino)Silane Precursor as a Control Using $N_2$ without $NH_3$ The procedure of Example 5 was followed with the exception of the precursor and it was used as a control. BTBAS is a precursor used in production processes worldwide and it was chosen as the representative aminosilane comparison because of its well accepted performance characteristics.

10 sccm of bis(tertiary butylaminosilane) (BTBAS) was flowed into a reactor at 570° C. with 20 sccm He and 20 sccm $N_2$ at 1.0 Torr (133 Pa) for a deposition time of 70 minutes. These films have only 20% of the stress and less than 10% of the etch resistance of the mono-aminosilanes (See Table 1).

FIG. 1 was generated using the stress data with respect to bis(tertiary butylaminosilane) and diethylaminosilane. It shows the results of stress measurements using an FSM system. The results for diethylaminosilane were unexpected, i.e., a high stress at a low $NH_3$:DEAS ratio was achieved including that of maintaining a high stress modest $NH_3$:DEAS ratios.

Precursors such as bis(tertiarybutylamino)silane and dichlorosilane produce films that have decreasing stresses as the ammonia to chemical ratio is decreased. At a low NH3:BTBAS ratio stress results are poor. Reducing the ammonia for these precursors creates a silicon rich film and this reduces the thermal expansion coefficients of these films relative to the silicon substrate. Although not intending to be bound by theory, reducing the ammonia:DEAS ratio in the deposition process increases the Si to N atomic ratio, the effect is that the C to Si atomic ratio increases. Apparently, then, there is some replacement of Si—N with Si—C bonds and these bonds result in producing films having similar stress.

Figure 2:
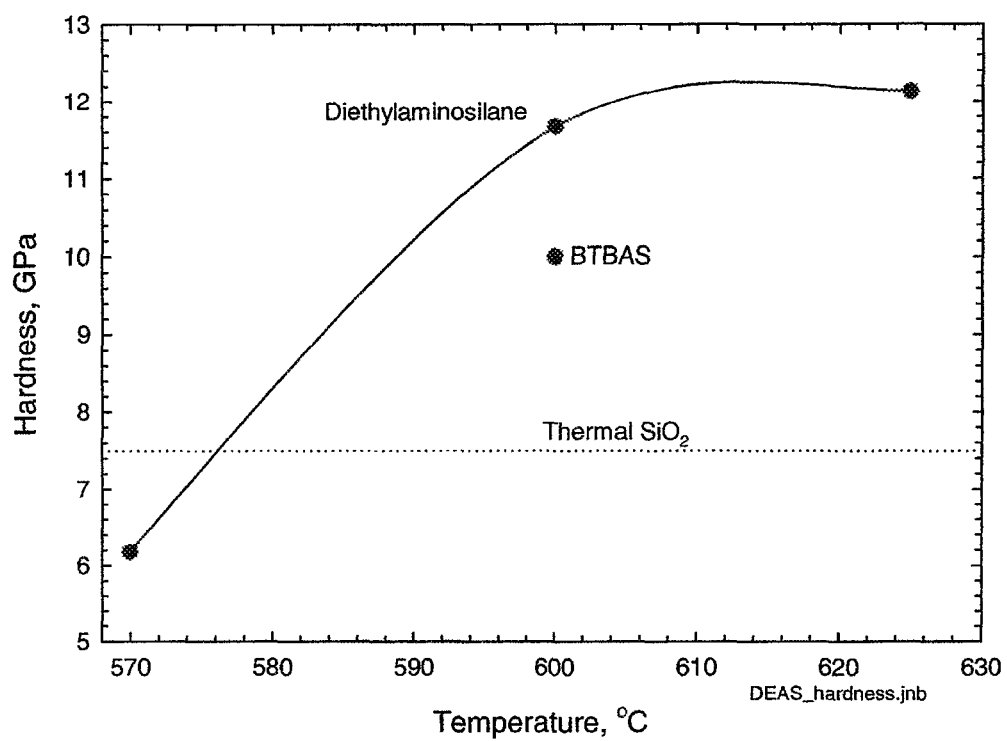
FIG. 2 is a plot of the hardness of films formed by the deposition of diethylaminosilane and bis(tertiary)butylaminosilane as a function of the temperature in the deposition process against a standard $SiO_2$.

A second component of the example was the measurement of film hardness. It was measured by indentation using a Hysitron system. FIG. 2 is a plot which shows the deposited film hardness. When diethylaminosilane was used as the precursor as compared to a BTBAS deposition and to thermally grown silicon dioxide harder films were obtained. Harder films are more protective of underlying layers and themselves in chemical-mechanical polishing (CMP) operations. This property, too, was surprising.

Example 9

Etch Resistance of Silicon Nitride and Silicon Carbo-Nitride Films

In this example, the results of etching of various silicon nitride and silicon carbo-nitride films are set forth in Table 1. Table 1 displays the results of etching films from several precursors in 1% (of 49%) HF. The etch rates are given relative to those of thermally grown silicon dioxide that were etched at the same time. The lower the etch rate of a film, the better it is for maintaining geometries and protecting underlying layers as undesired silicon dioxide is removed.

TABLE 1

| Chemical | NH$_3$ ratio | Deposition Temperature, ° C. | 1% HF Etch Rate Relative to SiO$_2$ |
| --- | --- | --- | --- |
| BTBAS | 2:1 | 570 | 0.188 |
| BTBAS | 0 | 570 | 0.018 |
| DEAS | 2:1 | 570 | 0.006 |
| DEAS | 4:1 | 570 | 0.008 |
| DEAS | 1:1 | 570 | 0.009 |
| DEAS | 0 | 570 | 0.001 |
| DIPAS | 2:1 | 570 | 0.006 |
| DIPAS | 0 | 570 | 0.006 |

BTBAS = bis(tertiarybutylamino)silane
DEAS = diethylaminosilane
DIPAS = diisopropylaminosilane
Comparison of film etch rates in 1% of 49% HF at 24° C.

From the above Table 1, DEAS is shown to have excellent low etch rates at NH$_3$ to precursor ratios of from 0 to 2. On the other hand, a ratio of NH$_3$:BTBAS, even at an NH$_3$:BTBAS ratio of 0:1:1 gave higher etch rates, than DEAS at a 2:1 ratio. Excellent low etch rates are shown at low NH$_3$:BTBAS ratios, but recall with BTBAS stress levels are poor at the low NH$_3$:BTBAS level.

Summarizing, dielectric silicon carbo-nitride films of the formula, Si$_x$C$_y$N$_z$, can be produced from the classes of aminosilanes as described, by CVD and other deposition processes. It is believed the high activity of the SiH$_3$ group allows for the production of Si$_x$C$_y$N$_z$ film depositions at temperatures as low as 550° C. whereas many of the precursors for forming Si$_x$C$_y$N$_z$ films do not perform well.

It is believed, also, the low steric hindrance for the ammonia transamination reaction on the silicon center allows these compounds to react with ammonia and form films with increasing nitrogen concentrations at relatively low temperatures. Ligands such as ethyl, isopropyl, butyl, etc. act as good leaving groups as they become volatile byproducts by beta-hydride elimination. Any carbon left behind is bonded to silicon. In contrast, aminosilane precursors which have methyl groups as reported in the past do not have this dissociation route. They remain bonded to the nitrogen and can be incorporated and trapped in the growing film. The presence of such trapped methyl groups are easily distinguished in infrared spectra (see FIG. 3). Here, though, the absence of a C—H peak in FIG. 3 indicates that there can be only be a very low level of hydrocarbon trapped in the film.

The invention claimed is:

1. An aminosilane compound selected from the group having the following formulas:

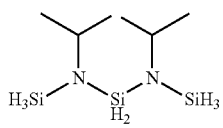

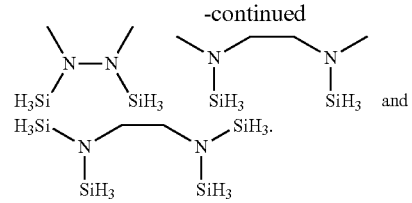

2. The aminosilane of claim 1 comprising:

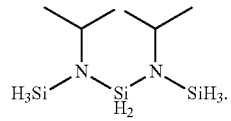

3. A composition comprising:

and at least one member selected from the group consisting of nitrogen, ammonia, hydrazine, and dimethylhydrazine.

4. The aminosilane of claim 1 comprising:

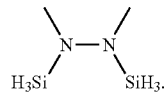

5. The aminosilane of claim 1 comprising:

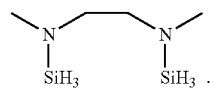

6. The aminosilane of claim 1 comprising:

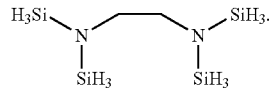

7. A composition comprising the compound of claim 1 and at least one aminosilane compound selected from the group consisting of:

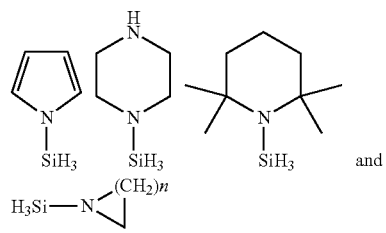

and where n is 4 or 5.

8. The composition of claim 7 comprising:

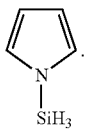

9. The composition of claim 7 comprising:

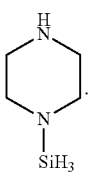

10. The composition of claim 7 comprising:

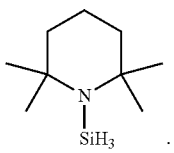

11. The composition of claim 7 comprising:

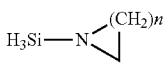

wherein n is 4 or 5.

12. A composition comprising the compound of claim 1 and at least one member selected from the group consisting of:

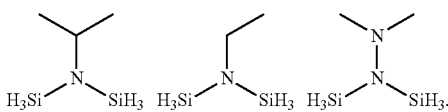

13. The composition of claim 12 comprising:

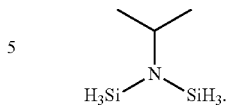

14. The composition of claim 12 comprising:

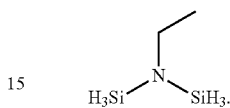

15. The composition of claim 12 comprising:

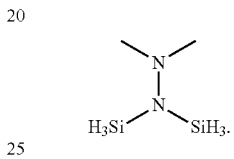

16. A composition comprising at least one aminosilane selected from the group consisting of:

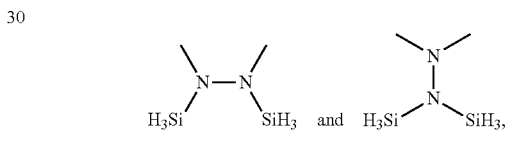

and at least one member selected from the group consisting of nitrogen, ammonia, hydrazine, and dimethylhydrazine.

17. A composition comprising the compound of claim 1 and at least one member selected from the group consisting of bis-tert-butylaminosilane, tris-iso-propylaminosilane, bis-diethylaminosilane, tris-dimethylaminosilane, and bis-iso-propylaminosilane.

18. A composition comprising the compound of claim 1 and at least one member selected from the group consisting of nitrogen, ammonia, hydrazine, and dimethylhydrazine.

* * * * *